United States Patent [19]
König et al.

[11] Patent Number: 5,705,594
[45] Date of Patent: Jan. 6, 1998

[54] POLYAMINE CROSSLINKING AGENT FORMULATION AND ITS PREPARATION

[75] Inventors: Klaus König, Odenthal; Otto Neuner, Bergisch Gladbach; Werner Rasshofer, Köln, all of Germany

[73] Assignee: Bayer Aktiengesellschaft, Leverkusen, Germany

[21] Appl. No.: 767,564

[22] Filed: Dec. 16, 1996

[30] Foreign Application Priority Data

Dec. 21, 1995 [DE] Germany ............... 195 48 026.0

[51] Int. Cl.$^6$ ............... C08G 18/08; C08G 18/10
[52] U.S. Cl. ............... 528/60; 528/48; 528/53; 528/73; 528/183; 528/222; 528/229; 544/180
[58] Field of Search ............... 544/180; 528/48, 528/53, 60, 73, 183, 222, 229

[56] References Cited

U.S. PATENT DOCUMENTS

| | | | |
|---|---|---|---|
| 2,801,244 | 7/1957 | Balon | 544/222 |
| 4,115,373 | 9/1978 | Henes et al. | 528/48 |
| 4,525,534 | 6/1985 | Rasshofer | 525/127 |
| 4,783,345 | 11/1988 | Kleeberg et al. | 427/96 |
| 4,812,490 | 3/1989 | Kleeberg et al. | 523/443 |

FOREIGN PATENT DOCUMENTS

| | | |
|---|---|---|
| 0048369 | 3/1982 | European Pat. Off. . |
| 48369 | 3/1982 | European Pat. Off. . |
| 0271772 | 6/1988 | European Pat. Off. . |
| 0274646 | 7/1988 | European Pat. Off. . |
| 2551634 | 6/1977 | Germany . |
| 3227219 | 2/1984 | Germany . |

*Primary Examiner*—Richard L. Raymond
*Attorney, Agent, or Firm*—Sprung Kramer Schaefer & Briscoe

[57] ABSTRACT

Liquid polyamine crosslinking agent formulations based on trimerized toluylene 2,4- and/or 2,6-diisocyanate, with formation of an isocyanurate structure and hydrolysis of the isocyanate groups to amine groups, are described. The novel crosslinking agent formulations have a content of 40 to 80% of the total weight of the solids content of the crosslinking agent formulation of 1,3,5-tris-(3-amino-4-methyl-phenyl, 2-methyl-3-aminophenyl) isocyanurate (I) which is not further condensed, and a content of not more than 1.0% of the total weight of the crosslinking agent formulations of toluylene-2,4- and/or -2,6-diamine (III). For the preparation, toluylene diisocyanate is trimerized, to form the isocyanurate structure, until 10 to 25% of the NCO groups have been reacted. The toluylene diisocyanate which has not undergone condensation is then distilled off, the bottom product formed by this operation is taken up directly in a solvent A and the 30 to 70% strength by weight solution formed by this procedure is metered into a hydrolysis in water/N,N-dialkyl-carboxylic acid amide in the presence of a catalytic amount of a basic catalyst. After the hydrolysis, the crosslinking agent formulations are brought to a solids content of 35 to 60% of the total weight of the formulation by distilling off a portion of the solvents and adding a solvent B.

19 Claims, No Drawings

POLYAMINE CROSSLINKING AGENT FORMULATION AND ITS PREPARATION

BACKGROUND OF THE INVENTION

1. Field of the Invention

The invention relates to a liquid polyamine crosslinking agent formulation with a solids content based on trimerized toluylene 2,4- and/or 2,6-diisocyanate, the isocyanate groups of which have been converted into amino groups, and having a high content of the trimer with the isocyanurate structure which is not condensed further and a very low content of toluylene-2,4- and/or -2,6-diamine. The invention furthermore relates to a process for the preparation of such a crosslinking agent formulation.

Polyamine crosslinking agents are of industrial importance as crosslinking agents and hardeners for the production of prepregs and of resin compositions based on epoxides. For production of prepregs, reinforcing materials are impregnated with polyepoxy resins and solutions of the crosslinking agent formulation, and can be cured by means of heat, while shaping, if appropriate after storage. In the production of resin compositions in the various industrial fields, in particular for encasing semiconductor structural elements and electronic and electrical circuits, these compositions likewise being curable by means of heat, polyepoxy resins and polyamine crosslinking agents are in general premixed with one another in the dry form and melted and then employed as a casting resin. However, solutions of polyepoxy resin and crosslinking agent can also be used for this purpose, solvents such as acetone, ethyl acetate, methyl ethyl ketone, 2-methoxy-ethanol and others, in particular the ketones mentioned, being employed. Solutions (formulations) of the crosslinking agents for this use form typically comprise 40 to 60% by weight of crosslinking agent in the total solution. When such solutions are used for casting, the solvent is removed at the use temperature, if appropriate under reduced pressure. The possible polyepoxy resins and any further substances, such as fillers, dyestuffs and, if appropriate, other amine hardener components, for this field of use are also known to the expert.

2. Description of the Related Art

Polyamine crosslinking agents which are similar to those according to the invention and the possible intended uses are already known, for example from EP-A 271 772 and EP-A 274 646 for the production of resin compositions and prepregs from polyepoxy resins.

The envisaged aim for production of a polyamine based on toluylene diisocyanate is that of condensation to give a triisocyanate having the isocyanurate structure and subsequent conversion of the NCO groups into amino groups according to the following reaction equation:

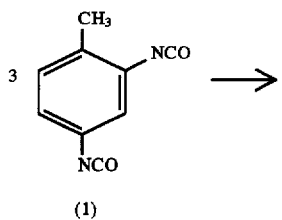

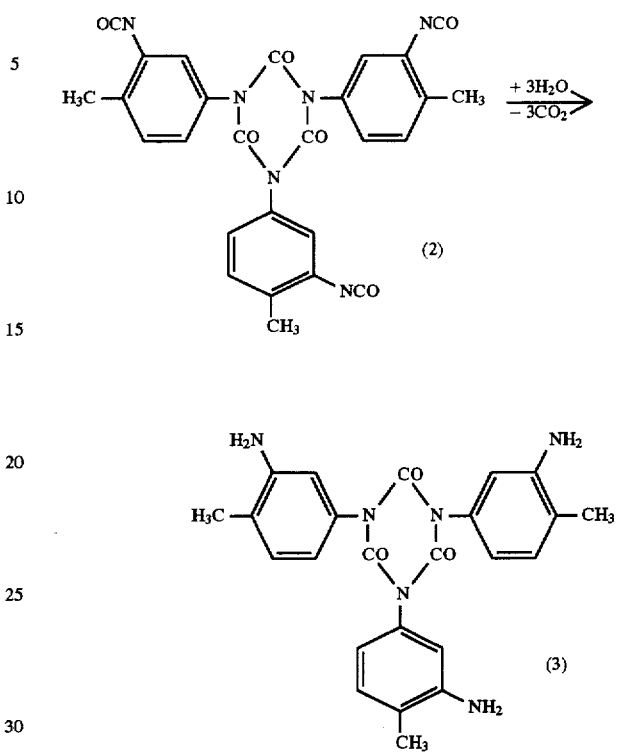

This equation shows, using the example of toluylene 2,4-diisocyanate (1), molecular weight 174.16, NCO content 48.25% by weight, trimerization to give 1,3,5-tris-(3-isocyanato-4-methyl-phenyl) isocyanurate (2), molecular weight 522.49, NCO 24.13% by weight, and hydrolysis thereof, $CO_2$ being split off, to give the corresponding 1,3,5-tris(3-amino-4-methyl-phenyl) isocyanurate (3), molecular weight 444.50, $NH_2$ content 10.81% by weight. (2) and its preparation by trimerization of (1) are known from U.S. Pat. No. 2,801,244. The hydrolysis of (2) to give (3) with water, for example in dimethylformamide (DMF) as a solvent, is likewise already known, for example from DE-A 32 27 219 and EP-A 271 772. However, the reaction sequence of (1) via (2) to (3) outlined above and its description in the abovementioned patent literature are merely idealized, and are not achieved in practice, since numerous polymer-homologous reactions and side reactions necessarily occur. Thus, it is found that the condensation of, for example, (1) (analogous statements also apply to position isomers of (1), such as, for example, toluylene-2,6-diisocyanate) does not stop at the trimer (2) of the above idealized description, but that the NCO groups present on the substituents of the isocyanurate ring in turn can undergo further condensation with diisocyanates (1) or even with further trimer which has already formed. This is shown in the following, likewise simplified and idealized again:

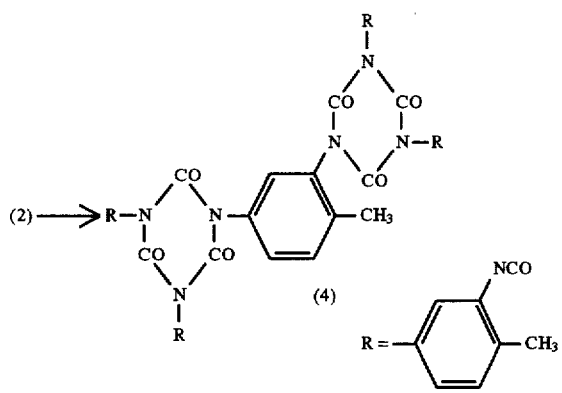

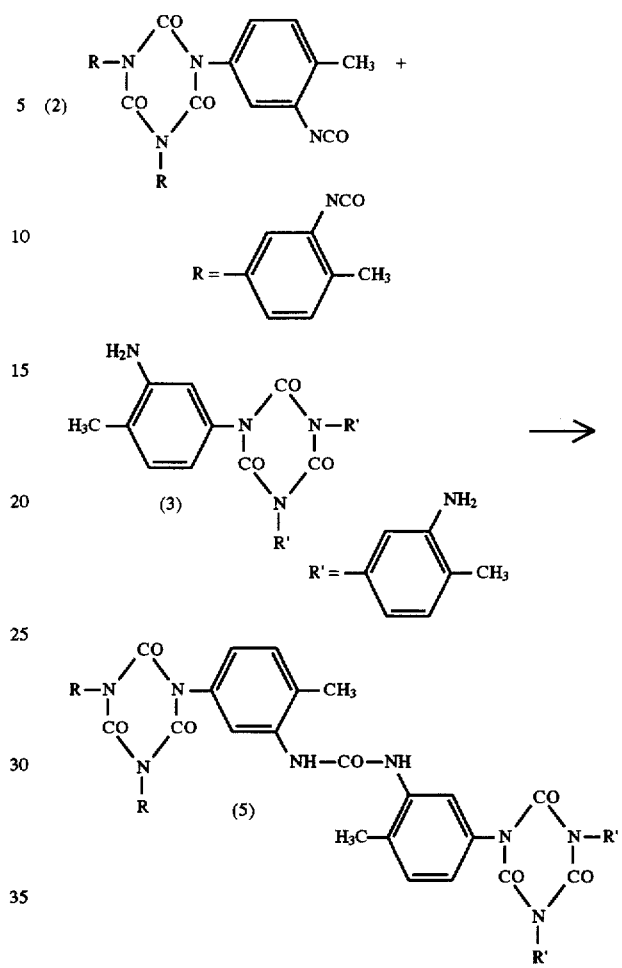

Such further condensation of course takes place with consumption of isocyanate groups, which can then no longer also be present as amino groups after the hydrolysis. As a result, the NCO content or the NH₂ content, desired after the hydrolysis, of a polyamine crosslinking agent drops, the functionality of the individual molecules of higher degree of condensation increasing. However, due to the accompanying increase in the molecular weight of such further condensates, the viscosity of the crosslinking agent increases in an undesirable manner and in a form which is undesirable and difficult for use. Thus, overall, the content of condensates having only one isocyanurate ring drops, while at the same time the amount of further condensates having 2 to 6 isocyanurate rings or (although to only a minor extent) the amount of further condensates having 7 to 10 or more isocyanurate rings increases (degrees of condensation of 2 to 6, 7 to 10 or higher). In addition to the poorer general ease of handling as a result of the increases in viscosity which have occurred due to the further condensation, the accuracy of the analytical determination of the functional groups also drops, this on the other hand representing the sole recipe basis for the uses described above because of the unclearness of the further condensation. However, the accessibility of the functional groups, even if these are still accessible for analytical determination, drops in the crosslinking agent for stearic reasons, so that in principle the functional groups present cannot participate to the full extent in the crosslinking/curing of resin mixtures.

Another disadvantage of crosslinking agents having contents of more highly functional (more highly condensed) molecules occurs if a precursor of epoxy resin and crosslinking agent is prepared on glass fiber mats or other reinforcing agents and, after evaporation of these solvents, this precursor is initially brought only into a precured state (so-called "B state") by heating, in order to obtain a storable semi-finished product, which is finally processed only in a second stage by compression molding in molds heated to high temperatures. Highly functional crosslinker contents here cause too little leeway between high tackiness, which makes removal of the semi-finished product from the mold difficult, and too intense pre-crosslinking, which causes trouble during final processing.

The hydrolysis is furthermore a very sensitive stage in the production of polyamine crosslinking agents of the type described here. In particular, in addition to isocyanate which has not yet been hydrolyzed, amino groups which have already been formed by hydrolysis are present within small units of time. However, these amino groups are extremely reactive with respect to isocyanate groups, with which they react to form urea groups. This is shown in simplified form by the following equation:

This urea formation also represents a substantial loss of functional groups, the functionality of the individual molecules (in this case (5) of degree of condensation 2) in turn rising, and is therefore also capable of forcing the viscosity further upward in an undesirable manner. Finally, under intensive hydrolysis conditions, the possibility of hydrolytically cleavage of the isocyanurate ring must also be expected, which results in further complications.

To avoid the abovementioned undesirable urea formation during hydrolysis of (2) it has already been reported that condensates which, in the idealized form, contain (2) as the main component can first be reacted with benzyl alcohol to give the associated poly-benzylurethane, which is then reacted further by catalytic hydrogenation to give the polyamine of the idealized form (3), toluene and CO₂ (EP-A 0 048 369). However, this possibility requires great effort and is very expensive, and requires handling of the high-boiling substance benzyl alcohol which is foreign to the system.

If the intention was to suppress the further condensation described above to give higher molecular weight and high-viscosity condensates with a larger number of cyanurate rings, the condensation would have to be interrupted earlier. However, this carries the risk of the content of toluylene 2,4- and/or 2,6-diisocyanate included in the condensation. Toluylenediamine is formed from this, however, during the hydrolysis, and this product, as is also the case with other primary aromatic amines, is dangerous to health.

The present invention overcomes the disadvantages mentioned by providing polyamine crosslinking agent formulations having an increased content of trimer (3), based on the total weight of the crosslinking agent mixture, and at the same time an extremely low content of toluylenediamine. Only as a result of this does its industrial use, which it has not yet been possible to realize with polyamine crosslinking agents of this type described to date, become possible.

SUMMARY OF THE INVENTION

The invention relates to liquid polyamine crosslinking agent formulations with a solids content based on triamine of the formula

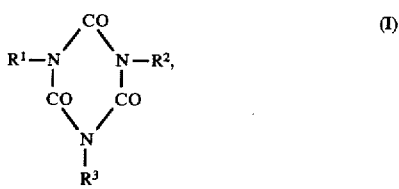

in which
$R^1, R^2$ and $R^3$ independently of one another denote 2-methyl-3-amino-phenyl or 3-amino-4-methyl-phenyl, formed by hydrolysis of the trimerized toluylene diisocyanate on which they are based, of the formula

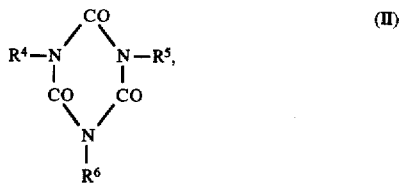

in which
$R^4, R^5$ and $R^6$ independently of one another denote 2-methyl-3-isocyanatophenyl or 3-isocyanato-4-methyl-phenyl,
which have a content of 40 to 80% of the total weight of the solids content of crosslinking agent formulations of triamine (I) with the degree of condensation 1, expressed by the number of isocyanurate nuclei, and a content of not more than 1.0% of the total weight of the solids content of the crosslinking agent formulations of toluylenediamines of the formula

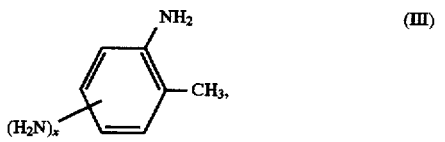

in which
x indicates the 2- or 4-position relative to the methyl group, the remainder to make up 100% of the solids content being condensates of higher degree of condensation, the solids content being 35 to 60% of the total weight of the formulations and the remainder to make up 100% of the total weight being a solvent mixture which is an N,N-dialkyl-carboxylic acid amide to the extent of 20 to 40% by weight of the solvent mixture and an ester or ketone for the remainder.

DETAILED DESCRIPTION OF THE INVENTION

The crosslinking agent formulations according to the invention preferably have a content of 50 to 65% of the total weight of the solids content of the crosslinking agent formulations of triamine (I). Also preferably, the crosslinking agent formulations according to the invention comprise a maximum content of 0.8%, particularly preferably not more than 0.5%, of diamine (III), based on the total weight of the solids content of the crosslinking agent formulations. The higher condensates which represent the remainder of the solids content are chiefly those having degrees of condensation of 2 and 3, rapidly decreasing amounts with degrees of condensation of 4 to 6 and only minor amounts of even higher condensates.

This is in marked contrast to crosslinking agents based on (I) of the prior art, which either have a content of (I) of only about 10 to 20% by weight, but 80 to 90% by weight of higher condensates with degrees of condensation of 2 to more than 10, or, with higher contents of (I), at the same time have a content of (III) which is too high and unacceptable for industrial hygiene reasons.

The crosslinking agent formulations according to the invention are in the form of a clear 35 to 60% strength by weight, preferably 40 to 55% strength by weight, solution, the solvent comprising, based on the total amount of solvent, an N,N-dialkyl-carboxylic acid amide to the extent of 20 to 40% by weight, preferably 30 to 35% by weight, and a ketone or an ester, preferably one having a boiling point of not more than 155° C., to the extent of 60 to 80%, preferably 65 to 70%.

The invention furthermore relates to a process for the preparation of liquid polyamine crosslinking agent formulations of the abovementioned type, which comprises a) in a first step, subjecting toluylene diisocyanate of the formula

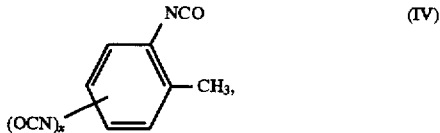

in which x has the above meaning, to a condensation reaction at a temperature of 20° to 100° C. in the presence of a first basic catalyst to form isocyanurate rings according to formula (I) until 10 to 25%, preferably 12 to 20%, of the NCO groups have been reacted, b) from the condensate of step a), after deactivation of the first basic catalyst by means of Lewis acids, removing the non-condensed (IV) by distillation at a heating medium temperature of 150° to 200° C. under 0.1 to 50 mbar down to a residual content of not more than 1%, preferably not more than 0.8%, particularly preferably not more than 0.5%, of the amount of (IV) employed in step a), c) taking up the bottom product of the distillation of step b) directly in a solvent A from the group consisting of esters, ketones, aromatic hydrocarbons or mixtures of several of these in an amount such that a 30 to 70% strength by weight solution of the bottom product forms, d) metering the bottom product solution obtained in step c) into a mixture of water, a catalytic amount of a second basic catalyst and an N,N-dialkyl-carboxylic acid amide at 70° to 120° C., preferably 80° to 100° C., particularly preferably 90° to 95° C., and during this operation hydrolyzing NCO groups to $NH_2$ groups and $CO_2$, the mount of $H_2O$ being 100 to 500 mol%, preferably 200 to 400 mol%, based on the amount of NCO equivalents in the bottom product of step b), and the amount of N,N-dialkyl-carboxylic acid amide being 3 to 15 times, preferably 5 to 12 times the bottom product, and e) by distilling of a portion of the solvents, obtaining the polyamine crosslinking agent as a concentrated solution, which is adjusted to the abovementioned solids content by addition of a solvent B from the group consisting of ketone and esters.

According to the invention, toluylene 2,4- and 2,6-diisocyanate and their mixtures, in particular in their industrially available qualities, can be employed as the toluylene diisocyanate (IV).

The condensation in process step a) is carried out at a temperature of 20° to 100° C., preferably 40° to 60° C., in the presence of a first basic catalyst from the group consisting of alkali metal hydroxides, carbonates and $C_1$–$C_{10}$-carboxylates and of quaternary ammonium bases, phosphonium bases and Mannich bases. Examples of such first basic catalysts are: NaOH KOH, $Na_2CO_3$, $K_2CO_3$, HCOONa, HCOOK, $CH_3COONa$, $CH_3COOK$ and Na and K salts of other aliphatic carboxylic acids having up to 10 C atoms, and furthermore tetramethyl-, tetraethyl- and tetrabutyl-ammoniumhydroxide, quaternary ammonium hydroxides having one long $C_6$–$C_{18}$-alkyl radical or the phenyl or benzyl radical and 3 $C_1$–$C_4$-alkyl radicals, which can also differ from one another, and furthermore quaternary ammonium hydroxides having 2 long-chain $C_6$–$C_{18}$-alkyl radicals or two phenyl or benzyl radicals and two $C_1$–$C_4$-alkyl radicals, and furthermore quaternary ammonium hydroxides which contain hydroxyalkyl groups or ether groups with terminal hydroxyl, and furthermore the Mannich bases obtainable from phenol, substituted phenol, bisphenols and ketones by reaction with formaldehyde and ammonia or primary or secondary amines, such as HO—$C_6H_4$—$CH_2$—$N(CH_3)_2$ (Houben-Weyl, Methoden der Organischen Chemie [Methods of Organic Chemistry], Volume XI/1 (1957), page 756 et seq.; DE-A 25 51 634). All these basic catalysts are known to the expert. The Mannich bases and the quaternary ammonium hydroxides are preferably employed, and the Mannich bases are particularly preferably employed. Catalytic amounts here are 0.0005 to 0.01 equivalent of basic catalyst, preferably 0.001 to 0.005 equivalent, per NCO equivalent.

The condensation of (IV) in process step a) is continued until 10 to 25%, preferably 12 to 20%, of the NCO groups have been reacted; this can be ensured by sampling from the reaction mixture and analysis.

In a process step b), the first basic catalyst is then deactivated by means of Lewis acids or alkylating/acylating agents, such as methyl o-/p-toluenesulfonate, dimethyl sulfate, benzoyl chloride, acetylchloride or analogous compounds, in an equivalent amount or an amount up to 20 equivalent-% more, and the (IV) which has not undergone condensation in step a) is distilled off down to a residual content of not more than 1%, preferably not more than 0.8%, particularly preferably not more than 0.5%, of its initial amount. This is carried out at a temperature for the heating medium in the distillation apparatus, with a heating jacket, heating coils or similar indirect heating of 150° to 200° C., preferably 160° to 180° C., under a pressure of 0.1 to 50 mbar, preferably 0.1 to 20 mbar. The distillation can be carried out in one stage or in several stages under decreasing pressures in the various stages. A thin film evaporator, a spiral evaporator or a similar continuously operated distillation apparatus, for example, can be employed for this removal by distillation.

The bottom product obtained in reaction step b) is taken up directly in a solvent A in reaction step c). The solvent A is one from the group consisting of aliphatic esters, aliphatic ketones, aromatic hydrocarbons or a mixture of several of these, preferably having a boiling point of not more than 155° C. Examples are ethyl acetate, butyl acetate, methyl propionate, acetone, methyl ethyl ketone (MEK), methyl propyl ketone, methyl butyl ketone, benzene, toluene and the isomeric xylenes. Preferred solvents A are esters and ketones, particularly preferably ethyl acetate and MEK. The amount of solvent A is chosen such that a 30 to 70% strength by weight solution of the bottom product from stage b) is formed.

The bottom product solution obtained in reaction step c) is now introduced, in reaction step d), into a mixture of water, a catalytic amount of a second basic catalyst and an N,N-dialkyl-carboxylic acid amide, such as dimethylformamide (DMF), diethylformamide or dimethylacetamide (DMAc), preferably DMF, at 70° to 120° C., preferably 80° to 100° C., particularly preferably 90° to 95° C. The second basic catalyst is an alkali metal hydroxide, carbonate or $C_1$–$C_{10}$-carboxylate of the abovementioned type or an alkali metal bicarbonate. The NCO groups are hydrolyzed to $NH_2$ groups and $CO_2$ by this procedure. The amount of water in reaction step d) is 100 to 500 mol%, preferably 200 to 400 mol%, based on the amount of NCO equivalents in the bottom product of step b). The catalytic amount of second basic catalyst is, for example, 0.0005 to 0.01 equivalent, preferably 0.001 to 0.005 equivalent, of second basic catalyst per NCO equivalent in the bottom product of b). The amount of N,N-dialkyl-carboxylic acid amide is 3 to 15 times, preferably 5 to 12 times, the bottom product.

For carrying out the hydrolysis in reaction step d), the mixture of water, the second basic catalyst and the N,N-dialkyl-carboxylic acid amide is initially introduced into the reaction vessel and brought to the desired reaction temperature. The solution of the bottom product of reaction step b) is then metered into solvent A, with thorough stirring, such that the evolution of $CO_2$ which immediately starts is well-controlled. After the end of the evolution of $CO_2$ and an after-reaction time, a clear solution is obtained.

A polyamine crosslinking agent formulation according to the invention which is suitable for the production of prepregs or resin compositions is then obtained in step e) from the hydrolysis solution obtained by distilling off a portion of solvents A and of the N,N-dialkyl-carboxylic acid amide, any excess hydrolysis water also being distilled off. An approximately 70 to 85% strength by weight solution of the hydrolysis product can be formed by this procedure, and is brought to the abovementioned mentioned solids content by addition of a solvent B) from the group consisting of ketones and esters of the abovementioned type. Such formulations which are easy to handle and are particularly preferred for use in practice are those in which DMF and MEK (as solvent B) are present.

The polyamine crosslinking agent formulations according to the invention have a high content of at least 40% of the total of the solids content of triamine (I) with only one isocyanurate ring. At the same time, they comprise not more than 1% of the total weight of the solids content of toluylenediamine (III). The high content of mononuclear isocyanurate components has the effect of a low viscosity, which on the one hand results in a higher amount of functional groups compared with products which have been prepared by processes of the prior art. This higher content of functional groups allows economical use of the polyamine crosslinking agent formulation and therefore cheaper recipes for epoxy resin mixtures. The lower viscosity furthermore prevents premature solidification at a still low degree of

9 reaction between epoxide and amine groups in the resin mixtures mentioned. The preparation according to the invention of the polyamine crosslinking agent formulations allows a high degree of recovery of the solvents which do not remain in the liquid formulations.

EXAMPLES

Example 1a (Condensation)

1000 parts by weight of a mixture of 65% by weight of toluylene 2,4-diisocyanate and 35% by weight of toluylene 2,6-diisocyanate and 0.26 part by weight of the Mannich base prepared from phenol, dimethylamine and formaldehyde were mixed at 45° C. The trimerization which started immediately was continued at 45±2° C., while stirring and with exclusion of moisture, until the NCO content had fallen from originally 48.25 to 42% by weight. The trimerization was stopped by addition of 0.65 part by weight of methyl o-/p-toluenesulfonate and subsequent stirring at 60° C. for 1 hour. The excess monomeric isocyanate was distilled off in vacuo by means of a thin film evaporator. The resulting distillation bottom product comprised 0.3% by weight of free monomeric toluylene diisocyanate and 72% by weight of tris-(isocyanatotoluene) isocyanurate of degree of condensation 1. The distillation bottom product was taken up directly in the same mount of ethyl acetate.

Example 1b (Hydrolysis)

7300 g of dimethylformamide (DMF), 270 g of completely desalinated water (15 mol) and 0.8 g of NaOH in the form of a 50% strength aqueous solution were initially introduced into a 10 l reaction vessel with a stirrer, thermometer and effective reflux condenser, and were heated to 95° to 100° C., while stirring vigorously. 897.5 g of condensate (essentially trimer of degree of condensation 1; 5 equivalents of NCO) in the form of a 50% strength solution in ethyl acetate were metered into the vessel in the course of about 1 hour. After the evolution of $CO_2$ had ended, the mixture was subsequently stirred for a further 15 minutes and then cooled to 70° C. The ethyl acetate was then distilled off in the form of an azeotrope having the composition 91.9% of ethyl acetate and 8.1% of water under 200 mbar. The distillate separated into two phases, of which the upper phase comprised 96.6% of ethyl acetate and 3.4% of water and could be freed from the water by incipient distillation, so that the resulting ethyl acetate could be introduced again into the process. In addition to 90.4% of water, the lower phase also comprised 8.4% of ethyl acetate, 1% of DMF and further unidentified substances. This phase was also collected after several test runs and worked up for organic contents. The yields of ethyl acetate in a series of successive experiments was thus nearly 100%. The distillation bottom product was freed from the majority of DMF by further vacuum distillation (the DMF could be used in a subsequent batch without further purification), so that a solution of the polyamine crosslinking agent in DMF of 75% solids content was obtained. 90° to 100° C./10 mbar were the distillation conditions finally reached in this procedure. The vacuum was eliminated by addition of nitrogen into the distillation flask. After addition of 520 g of methyl ethyl ketone, a solution of the polyamine crosslinking agent mixture of about 50% by weight of solids, 16.6% by weight of DMF and 33.4% of MEK was obtained. The solution had an amine number of 158, which means an amine number of 316 or a content of 9.0% of $NH_2$ for the polyamine crosslinking agent mixture. The viscosity of the solution at 25° C. was 150 mPas. The solution had a pale brownish color.

10

What is claimed is:

1. A liquid polyamine crosslinking agent formulation with a solids content based on a triamine of the formula (I)

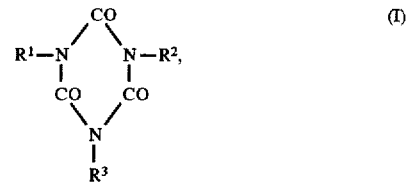

in which $R^1, R^2$ and $R^3$ independently of one another denote 2-methyl-3-amino-phenyl or 3-amino-4-methyl-phenyl, formed by hydrolysis of the trimerized toluylene diisocyanate on which it is based, of the formula

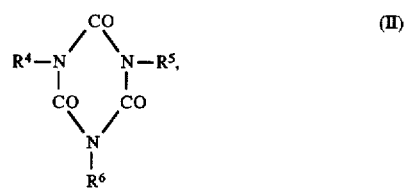

in which $R^4, R^5$ and $R^6$ independently of one another denote 2-methyl-3-isocyanato-phenyl or 3-isocyanato-4-methyl-phenyl, which has a content of 40 to 80% of the total weight of the solids content of crosslinking agent formulation of triamine (I) with the degree of condensation 1, expressed by the number of isocyanurate nuclei, and a content of not more than 1.0% of the total weight of the solids content of the cross-linking agent formulation of toluylenediamines of the formula

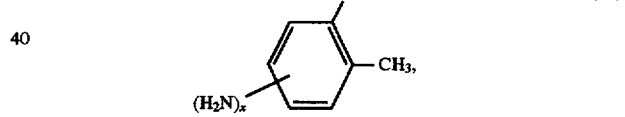

in which x indicates the 2- or 4-position relative to the methyl group, the remainder to make up 100% of the solids content being condensates of higher degree of condensation, the solids content being 35 to 60% of the total weight of the formulation and the remainder to make up 100% of the total weight being a solvent mixture which is an N,N-dialkyl-carboxylic acid amide to the extent of 20 to 40% by weight of the solvent mixture and an ester or ketone for the remainder.

2. The crosslinking agent formulation of claim 1, which has a content of 50 to 65% by weight of the solids content of triamine (I).

3. The crosslinking agent formulation of claim 1, which has a content of not more than 0.8% of the total weight of the solids content of toluylenediamine of the formula (III).

4. The crosslinking agent formulation of claim 3, which has a content of not more than 0.5% of the total weight of the solids content of the toluylenediamine of the formula (III).

5. The crosslinking agent formulation of claim 1, wherein the solids content is 40 to 55% of the total weight of the formulation.

6. The crosslinking agent formulation of claim 1, wherein the solvent mixture is a N,N-dialkyl-carboxylic acid to the extent of 30 to 35% by weight and an ester or ketone for the remainder.

7. The crosslinking agent formulation of claim 6, wherein the N,N-dialkyl-carboxylic acid amide is N,N-dimethylformamide.

8. The crosslinking agent formulation of claim 6, wherein the ester is ethyl acetate.

9. The crosslinking agent formulation of claim 6, wherein the ketone is methyl ethyl ketone.

10. A process for the preparation of a liquid polyamine crosslinking agent formulation of claim 1, which comprises
    a) a first step, subjecting toluylene diisocyanate of the formula

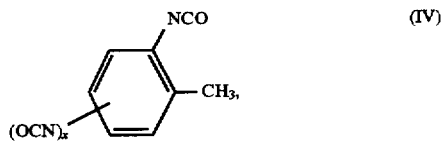

in which x has the meaning given in claim 1,
    to a condensation reaction at a temperature of 20° to 100° C. in the presence of a first basic catalyst to form isocyanurate rings according to formula (I) of claim 1, until 10 to 25% of the NCO groups have been reacted,
    b) from the condensate of step a), after deactivation of the first basic catalyst by means of Lewis acids, removing the non-condensed (IV) by distillation at a heating medium temperature of 150° to 200° C. under 0.1 to 50 mbar down to a residual content of not more than 1% of the amount of (IV) employed in step a),
    c) taking up the bottom product of the distillation of step b) directly in a solvent A from the group consisting of ester, ketones, aromatic hydrocarbons and mixtures of several of these in an amount such that a 30 to 70% strength by weight solution of the bottom product forms,
    d) metering the bottom product solution obtained in step c) into a mixture of water, a catalytic amount of a second basic catalyst and an N,N-dialkyl-carboxylic acid amide at 70° to 120° C., and during this operation hydrolyzing NCO groups to $NH_2$ groups and $CO_2$, the mount of $H_2O$ being 100 to 500 mol%, based on the amount of NCO equivalents in the bottom product of step b), and the amount of N,N-dialkyl-carboxylic acid amide being 3 to 15 times the bottom product, and
    e) by distilling of a portion of the solvents, obtaining the polyamine crosslinking agent as a concentrated solution, which is adjusted to the solids content mentioned in claim 1 by addition of a solvent B from the group consisting of ketones and esters.

11. The process of claim 10, wherein 12 to 20% of the NCO groups are reacted in step a).

12. The process of claim 10, wherein the non-condensed (IV) is removed by distillation down to a residual content of no more than 0.8% of the amount of (IV) employed in step a).

13. The process of claim 12, wherein the non-condensed (IV) is removed by distillation down to a residual content of no more than 0.5% of the amount of (IV) employed in step a).

14. The process of claim 10, wherein, in step d), metering of the bottom product solution obtained in step c) is carried out at 80° to 100° C.

15. The process of claim 14, wherein, in step d), metering of the bottom product solution obtained in step c) is carried out at 90° to 95° C.).

16. The process of claim 10, wherein the amount of $H_2O$ is 200 to 400 mol%, based on the amount of NCO equivalents.

17. The process of 10, wherein the distillation in step b) is carried out at a heating medium temperature of 160° to 180° C.

18. The process of 10, wherein the distillation in step b) is carried out under 0.1 to 20 mbar.

19. The process of 10, wherein the distilling off of a portion of the solvents in step e) results in a 70 to 85% strength by weight solution of the hydrolysis product.

* * * * *

UNITED STATES PATENT AND TRADEMARK OFFICE
CERTIFICATE OF CORRECTION

PATENT NO. : 5,705,594
DATED : January 6, 1998
INVENTOR(S) : Konig, et al.

It is certified that error appears in the above-indentified patent and that said Letters Patent is hereby corrected as shown below:

Col. 12, line 3   Delete " mount " and substitute
                  -- amount --

Signed and Sealed this

Seventeenth Day of November, 1998

Attest:

BRUCE LEHMAN

Attesting Officer        Commissioner of Patents and Trademarks